United States Patent [19]

Jahn et al.

[11] Patent Number: 4,617,050
[45] Date of Patent: Oct. 14, 1986

[54] CYCLOHEXANE-1,3-DIONE DERIVATIVES

[75] Inventors: Dieter Jahn, Edingen-Neckarhausen; Rainer Becker, Bad Durkheim; Michael Keil, Ludwigshafen; Walter Himmele, Walldorf; Bruno Wuerzer, Otterstadt, all of Fed. Rep. of Germany

[73] Assignee: BASF Aktiengesellschaft, Ludwigshafen, Fed. Rep. of Germany

[21] Appl. No.: 750,996

[22] Filed: Jul. 2, 1985

Related U.S. Application Data

[63] Continuation-in-part of Ser. No. 496,644, May 20, 1983, abandoned.

[30] Foreign Application Priority Data

May 22, 1982 [DE] Fed. Rep. of Germany ....... 3219315

[51] Int. Cl.$^4$ .................... A01N 37/44; A01N 35/06; C07C 131/02; C07C 131/10
[52] U.S. Cl. .......................................... 71/98; 71/106; 71/121; 560/116; 560/118; 564/256; 564/257; 564/300
[58] Field of Search ................ 560/116, 118; 564/256, 564/257, 300; 71/98, 106, 121

[56] References Cited

U.S. PATENT DOCUMENTS

| | | | |
|---|---|---|---|
| 4,249,937 | 2/1981 | Iwataki et al. | 71/97 |
| 4,427,440 | 1/1984 | von der Osten et al. | 71/98 X |
| 4,440,566 | 4/1984 | Luo | 560/125 |
| 4,515,729 | 5/1985 | Iwataki et al. | 564/300 X |
| 4,517,013 | 5/1985 | Becker et al. | 564/256 X |

FOREIGN PATENT DOCUMENTS

| | | | |
|---|---|---|---|
| 0046860 | 3/1982 | European Pat. Off. | 71/121 |
| 0070495 | 1/1983 | European Pat. Off. | 71/121 |
| 0019945 | 2/1979 | Japan | 71/121 |
| 1461170 | 1/1977 | United Kingdom . | |

Primary Examiner—Natalie Trousof
Assistant Examiner—Patricia M. Scott
Attorney, Agent, or Firm—Keil & Weinkauf

[57] ABSTRACT

Cyclohexane-1,3-dione derivatives of the formula I

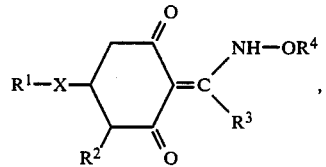

where $R^1$ is cycloalkyl of 3 to 12 carbon atoms which may or may not be olefinically monounsaturated to tetraunsaturated, can be substituted by not more than 3 methyl or ethyl groups, one vinyl, methylvinyl or allyl group, 1 or 2 chlorine atoms or one alkoxy group of 1 to 4 carbon atoms and can be bridged by an alkylene chain of not more than 4 carbon atoms, X is alkylene of 1 to 5 carbon atoms, which can be monounsaturated or diunsaturated, interrupted by not more than 2 sulfur or oxygen atoms and substituted by not more than 3 alkyl groups of 1 to 3 carbon atoms, $R^2$ is hydrogen of alkoxycarbonyl where alkoxy is of 1 to 2 carbon atoms, $R^3$ is alkyl of 1 to 4 carbon atoms, $R^4$ is alkyl of 1 to 3 carbon atoms, alkenyl of 3 or 4 carbon atoms, propargyl or haloalkenyl of 3 or 4 carbon atoms and 1 to 3 halogen atoms, and the salts of these compounds, processes for their preparation, herbicides containing these compounds, and their use.

3 Claims, No Drawings

CYCLOHEXANE-1,3-DIONE DERIVATIVES

This application is a continuation-in-part of application Ser. No. 496,644, filed on May 20, 1983, now abandoned.

The present invention relates to cyclohexane-1,3-dione derivatives, a process for the preparation of these compounds, herbicides which contain these compounds, and their use.

It has been disclosed that cyclohexane-1,3-dione derivatives, eg. the sodium salt of 2-(1-allyloxyaminobutylidene)-4-methoxycarbonyl-5,5-dimethylcyclohexane-1,3-dione (British Pat. No. 1,461,170), and 2-(1-ethoxyaminobutylidene)-5-(2-ethylthiopropyl)-cyclohexane-1,3-dione (U.S. Pat. No. 4,249,937) and 2-(1-allyloxyaminobutylidene)-5-cyclohexyl-cyclohexane-1,3-dione (Japanese Preliminary Published Application No. 54-19,945), can be used as herbicides. They are active mainly against gramineous weeds and gramineous crop plants and are also very well tolerated by broad-leaved crop plants, but not by cereals.

It is an object of the present invention to provide a herbicide which has a similar action against gramineous weeds and which can also be used in cereal crops.

We have found that this object is achieved by the cyclohexane-1,3-dione derivatives of the formula I as claimed in claim 1, and that these compounds and their salts have a herbicidal action against grasses, and cause little or no damage either to broad-leaved crop plants and monocotyledon crops not belonging to the family of grassses (Gramineae) or, surprisingly, to cereals.

The novel compounds can occur in a number of tautomeric forms, and the claims relate to all of these:

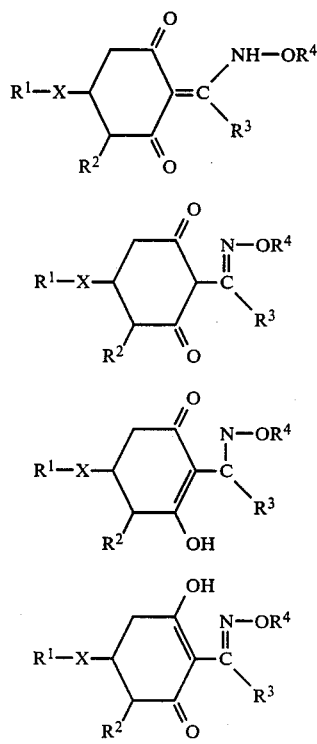

$R^1$ can be, for example, dichlorocyclopropyl, cyclopropyl, cyclopentyl, cyclohexyl, 2-methylcyclohexyl, 3-methylcyclohexyl, 4-methylcyclohexyl, cyclohex-3-enyl, 1-methylcyclohex-3-enyl, 2-methoxycyclohexyl, 3-(n-butoxy)-cyclohexyl, 4-isopropenylcyclohexyl, 2,2,6-trimethylcyclohexyl, 2,2,6-trimethylcyclohex-1-enyl, cycloheptyl, bicyclo[2.2.1]hept-2-yl, 2-methylbicyclo[2.2.1]hept-3-yl, 2,2-dimethylbicyclo[2.2.1]hept-3-yl, cyclooctyl, cyclododecyl or cyclododecadienyl.

X can be, for example, one of the following divalent radicals: methylene, methine, ethylene, methylethylene, vinylene, methylvinylene, ethylvinylene, propylene, tetramethylene, 1,3-butadienylene, 1,3-dimethyl-1,3-butadienylene, 1,3-diisopropyl-1,3-butadienylene, 1-methyl-3-isopropyl-1,3-butadienylene, 1,3-dimethylbut-1-enylene, 1,3-diisopropylbut-1-enylene, 2,4-dimethyltetramethylene, 2,4-diisopropyltetramethylene or 2-methyl-4-isopropyltetramethylene, or a divalent radical of the following formulae:

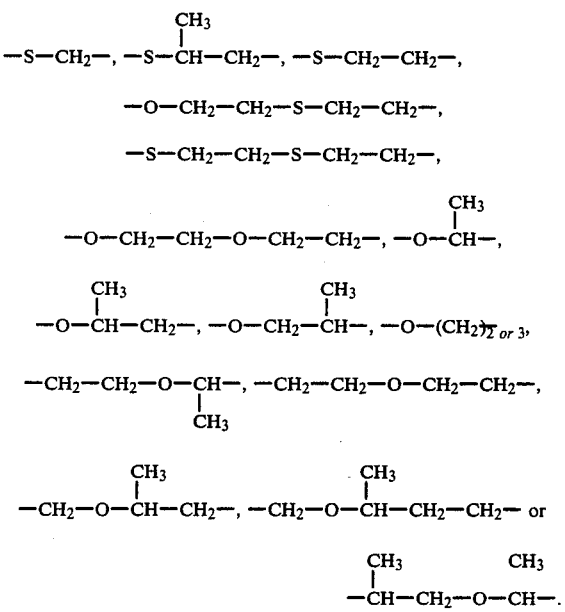

$R^2$ can be hydrogen, methoxycarbonyl or ethoxycarbonyl.

$R^3$ can be methyl, ethyl, n-propyl, i-propyl, n-butyl, sec.-butyl, i-butyl or tert.-butyl.

$R^4$ can be, for example, methyl, ethyl, n-propyl, i-propyl, allyl, propargyl, 3-chloroprop-2-enyl, 2-chloroprop-2-enyl, 2,3-dichloroprop-2-enyl or 2,3,3-trichloroprop-2-enyl.

The salts of the compounds are the metal and ammonium salts, preferably the alkali metal salts, in particular the potassium or sodium salts.

PREPARATION

The compounds according to the invention can be prepared by one of the following methods:

The starting compound used can be an aldehyde of the general formula $R^1$—X—CHO, and this compound can be prepared, in accordance with the equation below, by aldol condensation (see Organic Reactions, John Wiley & Sons, New York, 1968, Volume 16), if appropriate followed by selective hydrogenation of the double bond (see Houben-Weyl, Methoden der organ. Chemie, Volume IV/1c, Georg Thieme Verlag, Stuttgart—New York, 1980).

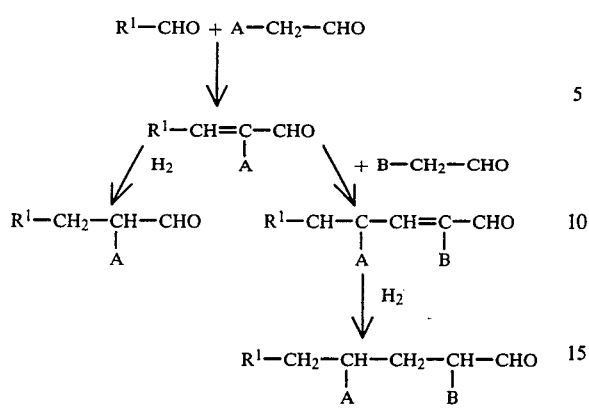

A and B are each identical or different alkyl chains of 1 to 3 carbon atoms. Either the saturated or the unsaturated aldehyde can be used for synthesis of the novel compounds.

Aldehydes having an ether structure can be obtained by hydroformylation of the corresponding enol-ethers.

Aldehydes having a thioether structure are obtained, for example, by an addition reaction of a mercaptan with an alpha, beta-unsaturated aldehyde.

If, in the formula $R^1$—X—CHO, X is methylethylene, the aldehyde intermediate can be prepared by hydroformylation of limonene. The configuration at the asymmetric carbon atom of the product obtained from R-limonene differs from that in the product obtained from S-limonene.

The aldehyde prepared by one of the above methods can be subjected to an aldol condensation with acetone to give the vinylketone III; isomers of the general formula IIIa are also frequently obtained.

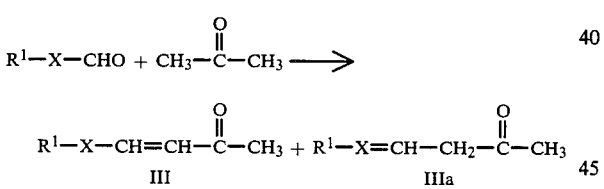

If X is methine, a vinylketone of the general formula III, or a mixture of this with IIIa, can be prepared from a cyclohexanone, in accordance with the following equation:

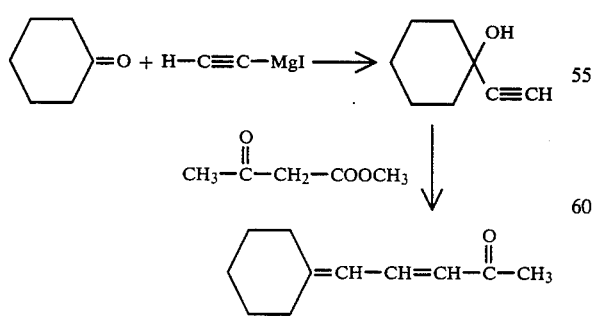

The vinylketone III can be reacted with a malonate, as described in, for example, Organic Synthesis Coll. Vol. II, page 200, to give a cyclohexane-1,3-dione of the general formula IV; the latter compound can also occur in the tautomeric forms IVa and IVb.

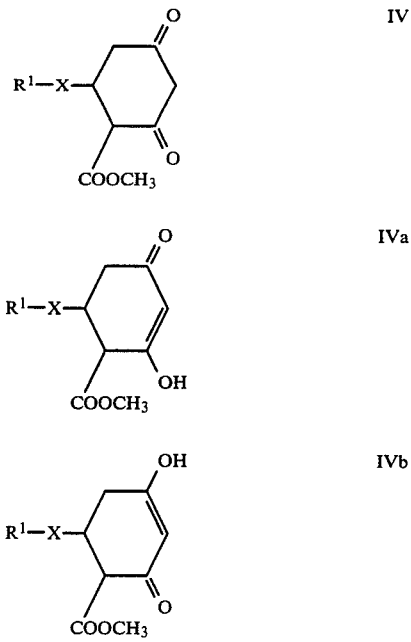

The cyclization may also be carried out using the isomers IIIa, since these isomerize under the reaction conditions. Another possible method of preparing the compounds IV from an aldehyde $R^1$—X—CHO comprises reaction with malonic acid by the Knoevenagel-Doebner method (cf. Org. Reactions, 15, 204), esterification of the resulting acid, and cyclization with an acetoacetate in a manner similar to that described in, for example, Houben-Weyl, Methoden der organischen Chemie, Volume 8, page 598.

This can be converted to a cyclohexane-1,3-dione of the general formula V, which can also occur in the tautomeric form Va, by boiling with a caustic alkali solution and heating the product in an acidic medium.

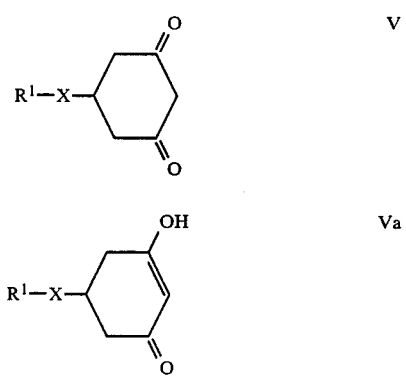

Compounds of the formulae IV and V can be converted to compounds of the formula II by the method described in, for example, L. DeBuyck et al. Tetrahedron Lett., 1975, 2491.

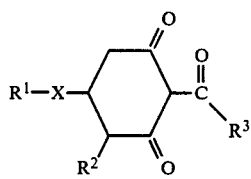

It is also possible to prepare compounds of the formula II via the enol-ester intermediates, which are obtained, possibly as isomer mixtures, in the conversion of the compounds of the formula V, and undergo rearrangement in the presence of an imidazole or pyridine derivative (cf. Japanese Pat. No. 54-063,052).

Compounds of the formula II can be converted to the compounds according to the invention by reaction with a hydroxylamine derivative $R^4$—$ONH_3Y$, wherein $R^4$ has the above meaning and Y is an anion. The reaction is advantageously carried out in the heterogeneous phase in an inert solvent at from 0° to 80° C. or boiling point of the mixture, preferably from 15° to 70° C., in the presence of a base. Examples of bases are carbonates, bicarbonates, acetates, alcoholates, hydroxides and oxides of alkali metals and alkaline earth metals, in particular sodium, potassium, magnesium and calcium. It is also possible to use an organic base, such as pyridine or a tertiary amine. A pH from 2 to 8, in particular from 4.5 to 5.5, is particularly suitable for the reaction. The pH for the reaction is preferably established by the addition of an acetate, for example an alkali metal acetate, in particular sodium acetate or potassium acetate, or a mixture of these. The amount of alkali metal acetate used is, for example, from 0.5 to 2 moles per mole of the ammonium compound. Examples of suitable solvents are methanol, ethanol, isopropanol, benzene, tetrahydrofuran, chloroform, acetonitrile, dichloroethane, ethyl acetate, dioxane and dimethylsulfoxide. The reaction is complete after a few hours. To isolate the product, the mixture is evaporated down, water is added, the aqueous phase is extracted with a non-polar solvent, and the solvent is distilled off under reduced pressure.

Furthermore, the novel compounds can be obtained by reacting a compound of the general formula II with a free hydroxylamine of the formula $R^4$—O—$NH_2$, where $R^4$ has the meanings stated in claim 1, in an inert solvent at from 0° C. to the boiling point of the mixture, preferably from 15° to 70° C. If appropriate, the alkylhydroxylamine is employed as an aqueous solution. Examples of suitable solvents are methanol, ethanol, isopropanol, cyclohexanol, methylene chloride, chloroform, toluene, tetrahydrofuran, acetonitrile, dichloroethane and ethyl acetate.

The sodium and potassium salts of the novel compounds can be obtained by treating these compounds with sodium or potassium hydroxide in aqueous solution or in an organic solvent, eg. methanol, ethanol or acetone.

The base used may also be a sodium or potassium alcoholate.

Other metal salts, eg. the manganese, copper, zinc, iron and barium salts, can be prepared by reacting the sodium salt with the corresponding metal chloride in aqueous solution.

In the Examples which follow, and illustrate the preparation of the novel cyclohexane-1,3-diones, parts are by weight unless stated otherwise. Parts by weight bear the same relation to parts by volume as that of the kilogram to the liter.

Preparation Examples

EXAMPLE 1

9.5 parts by weight of 2-butyryl-5-[2'-methyl-2'-(1"-methylcyclohex-1"-en-4-yl)-ethylene]-cyclohexane-1,3-dione, obtained by one of the above methods via hydroformylation of (+)-limonene, and 2.0 parts by weight of ethoxyamine in 100 parts of ethanol were stirred for 8 hours at room temperature, after which the solvent was distilled off under reduced pressure, the residue was taken up in 200 parts of dichloromethane, and the solution was washed with 5% strength hydrochloric acid, dried over sodium sulfate and evaporated down under reduced pressure. 2-(Ethoxyaminobutylidene)-5-[2'-methyl-2'-(1"-methylcyclohex-1"-en-4-yl)-ethylene]-cyclohexane-1,3-dione was obtained as an oil of the following formula (active ingredient No. 1):

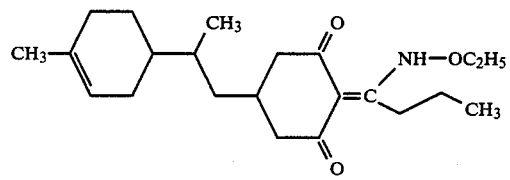

$n_D^{22}$: 1.5212
$C_{22}H_{35}NO_3$—
Calculated: C, 73.09; H, 9.76; N, 3.87. Found: C, 73.2; H, 9.7; N, 4.0.

EXAMPLE 2

5.8 parts by weight of 2-butyryl-5-(methinecyclohexylidene)-cyclohexane-1,3-dione, 2.4 parts by weight of allyloxyammonium chloride and 1.9 parts by weight of anhydrous sodium acetate in 150 parts by volume of ethanol were stirred for 12 hours at room temperature, after which the mixture was evaporated down under reduced pressure, the residue was stirred with 100 parts of dichloromethane and 100 parts of water, the organic phase was separated off, the aqueous phase was extracted with 50 parts of dichloromethane, and the combined organic phases were washed with water, dried over sodium sulfate and evaporated down under reduced prressure. 2-(Allyloxyaminobutylidene)-5-(methinecyclohexylidene)-cyclohexane-1,3-dione was obtained as an oil of the following formula (active ingredient No. 2):

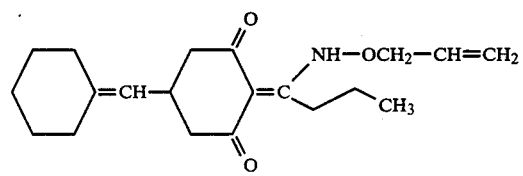

$n_D^{27}$: 1.5325
$C_{20}H_{29}NO_3$ (331)— Calculated: C, 72.47; H, 8.82; N, 4.23. Found: C, 72.7; H, 8.7; N, 4.3. .

The compounds below are obtained in a similar manner.

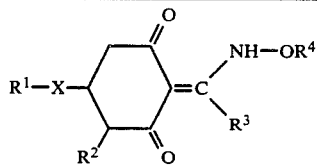

| No. | R¹ | X | R² | R³ | R⁴ | $n_D$ (at °C.) |
|---|---|---|---|---|---|---|
| 3 | cyclohexyl | methylene | H | n-$C_3H_7$ | $C_2H_5$ | 1.5150 (24) |
| 4 | cyclohexyl | methylene | $COOCH_3$ | n-$C_3H_7$ | $C_2H_5$ | 1.5073 (24) |
| 5 | cyclohexylidene | methine | H | n-$C_3H_7$ | $C_2H_5$ | 1.5266 (27) |
| 6 | cyclohexylidene | methine | $COOCH_3$ | n-$C_3H_7$ | $-CH_2-CH=CH_2$ | 1.5253 (29) |
| 7 | cyclohexylidene | methine | $COOCH_3$ | n-$C_3H_7$ | $C_2H_5$ | 1.5216 (29) |
| 8 | 3,3,5-trimethylcyclohexylidene | methine | H | $C_2H_5$ | $C_2H_5$ | |
| 9 | 3,3,5-trimethylcyclohexylidene | methine | H | $C_2H_5$ | $-CH_2-CH=CH_2$ | |
| 10 | 3,3,5-trimethylcyclohexylidene | methine | H | n-$C_3H_7$ | $C_2H_5$ | |
| 11 | 3,3,5-trimethylcyclohexylidene | methine | H | n-$C_3H_7$ | $-CH_2-CH=CH_2$ | |
| 12 | 2-cyclohexylcyclohexylidene | methine | H | $C_2H_5$ | $C_2H_5$ | |
| 13 | 2-cyclohexylcyclohexylidene | methine | H | $C_2H_5$ | $-CH_2-CH=CH_2$ | |
| 14 | 2-cyclohexylcyclohexylidene | methine | H | n-$C_3H_7$ | $C_2H_5$ | |
| 15 | 2-cyclohexylcyclohexylidene | methine | H | n-$C_3H_7$ | $-CH_2-CH=CH_2$ | |
| 16 | 2,2-dimethylbicyclo[2,2,1]-heptan-3-yl | methylene | H | $C_2H_5$ | $-C_2H_5$ | |
| 17 | 2,2-dimethylbicyclo[2,2,1]-heptan-3-yl | methylene | H | $C_2H_5$ | $-CH_2-CH=CH_2$ | |
| 18 | 2,2-dimethylbicyclo[2,2,1]-heptan-3-yl | methylene | H | n-$C_3H_7$ | $-C_2H_5$ | |
| 19 | 2,2-dimethylbicyclo[2,2,1]-heptan-3-yl | methylene | H | n-$C_3H_7$ | $-CH_2-CH=CH_2$ | |
| 20 | 1-methylcyclohexen-1-yl-4 | 2-methylethylene | H | n-$C_3H_7$ | $-CH_2-CH=CH_2$ | 1.5256 (22) |
| 21 | 1-methylcyclohexen-1-yl-4 | 2-methylethylene | H | $C_2H_5$ | $-C_2H_5$ | 1.5222 (25) |
| 22 | 1-methylcyclohexen-1-yl-4 | 2-methylethylene | H | $C_2H_5$ | $-CH_2-CH=CH_2$ | 1.5278 (25) |
| 23 | 1-methylcyclohexen-1-yl-4 | 2-methylethylene | $COOCH_3$ | n-$C_3H_7$ | $-C_2H_5$ | 1.5154 (29) |
| 24 | 1-methylcyclohexen-1-yl-4 | 2-methylethylene | $COOCH_3$ | n-$C_3H_7$ | $-CH_2-CH=CH_2$ | 1.5194 (30) |
| 25 | 1-methylcyclohexen-1-yl-4 | 2-methylethylene | H | n-$C_3H_7$ | $-CH_2-CH=CHCl$ | 1.5348 (21) |
| 26 | 1-methylcyclohexen-1-yl-4 | 2-methylethylene | H | n-$C_3H_7$ | $-CH_2-\underset{Cl}{C}=CH_2$ | |
| 27 | 1-methylcyclohexyl-4 | 2-methylethylene | $COOCH_3$ | n-$C_3H_7$ | $-CH_2-CH=CH_2$ | |
| 28 | 1-methylcyclohexyl-4 | 2-methylethylene | $COOCH_3$ | n-$C_3H_7$ | $-C_2H_5$ | |
| 29 | 1-methylcyclohexyl-4 | 2-methylethylene | H | n-$C_3H_7$ | $-CH_2-CH=CH_2$ | |
| 30 | 1-methylcyclohexyl-4 | 2-methylethylene | H | $C_2H_5$ | $-C_2H_5$ | |
| 31 | 1-methylcyclohexyl-4 | 2-methylethylene | H | $C_2H_5$ | $-CH_2-CH=CHCl$ | |
| 32 | 1-methylcyclohexyl-4 | 2-methylethylene | H | $C_2H_5$ | $-C_2H_5$ | |
| 33 | 1-methylcyclohexyl-4 | 2-methylethylene | H | $C_2H_5$ | $-CH_2-CH=CHCl$ | |
| 34 | cyclohexyl | 1-methylethylene | $COOCH_3$ | n-$C_3H_7$ | $-C_2H_5$ | |
| 35 | cyclohexyl | 1-methylethylene | $COOCH_3$ | n-$C_3H_7$ | $-CH_2-CH=CH_2$ | |
| 36 | cyclohexyl | 1-methylethylene | H | n-$C_3H_7$ | $-C_2H_5$ | 1.5143 (25) |
| 37 | cyclohexyl | 1-methylethylene | H | $C_2H_5$ | $-C_2H_5$ | |
| 38 | cyclohexyl | 1-methylethylene | H | $C_2H_5$ | $-CH_2-CH=CH_2$ | |
| 39 | cyclohexyl | 1-isopropylethylene | H | n-$C_3H_7$ | $-C_2H_5$ | |
| 40 | cyclohexyl | 1-isopropylethylene | H | n-$C_3H_7$ | $-CH_2-CH=CH_2$ | |
| 41 | cyclohexyl | 1,3-dimethylbutadien-1,3-ylene | H | n-$C_3H_7$ | $-C_2H_5$ | |
| 42 | cyclohexyl | 1,3-dimethylbutadien-1,3-ylene | H | n-$C_3H_7$ | $-CH_2-CH=CH_2$ | |
| 43 | cyclohexyl | 1,3-diisopropyl-butadien-1,3-ylene | H | n-$C_3H_7$ | $-C_2H_5$ | |
| 44 | cyclohexyl | 1,3-diisopropyl-butadien-1,3-ylene | H | $C_2H_5$ | $-CH_2-CH=CH_2$ | |
| 45 | cyclohexyl | 1-methyl-3-isopropyl-butadien-1,3-ylene | H | $C_2H_5$ | $-C_2H_5$ | |
| 46 | cyclohexyl | 1,3-dimethyltetra-methylene | H | n-$C_3H_7$ | $-C_2H_5$ | |
| 47 | cyclohexyl | 1,3-dimethyltetra-methylene | H | n-$C_3H_7$ | $-CH_2-CH=CH_2$ | |
| 48 | cyclohexyl | 1,3-diisopropyltetra-methylene | H | n-$C_3H_7$ | $-C_2H_5$ | |
| 49 | cyclohexyl | 1,3-diisopropyltetra-methylene | H | n-$C_3H_7$ | $-CH_2-CH=CH_2$ | |
| 50 | cyclohexyl | 1-methyl-3-isopropyl-tetramethylene | H | n-$C_3H_7$ | $-C_2H_5$ | |
| 51 | cyclohexen-1-yl-4 | 1-methylvinylene | H | n-$C_3H_7$ | $-C_2H_5$ | |
| 52 | cyclohexen-1-yl-4 | 1-methylvinylene | H | n-$C_3H_7$ | $-CH_2-CH=CH_2$ | |
| 53 | cyclohexen-1-yl-4 | 1-methylvinylene | H | $C_2H_5$ | $C_2H_5$ | |
| 54 | cyclohexen-1-yl-4 | 1-isopropylvinylene | H | n-$C_3H_7$ | $C_2H_5$ | |
| 55 | cyclohexen-1-yl-4 | 1-isopropylvinylene | H | n-$C_3H_7$ | $-CH_2-CH=CH_2$ | |
| 56 | cyclohexen-1-yl-4 | 1,3-dimethylbutadien-1,3-ylene | H | n-$C_3H_7$ | $C_2H_5$ | |
| 57 | cyclohexen-1-yl-4 | 1,3-dimethylbutadien- | H | n-$C_3H_7$ | $-CH_2-CH=CH_2$ | |

-continued

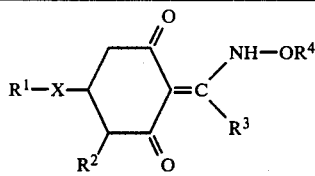

| No. | R¹ | X | R² | R³ | R⁴ | $n_D$ (at °C.) |
|---|---|---|---|---|---|---|
| 58 | cyclohexen-1-yl-4 | 1-methyl-3-isopropyl-butadien-1,3-ylene | H | n-$C_3H_7$ | $C_2H_5$ | |
| 59 | cyclohexen-1-yl-4 | 1-methyl-3-isopropyl-butadien-1,3-ylene | H | n-$C_3H_7$ | $-CH_2-CH=CH_2$ | |
| 60 | cyclohexen-1-yl-4 | 1-isopropyl-3-methyl-butadien-1,3-ylene | H | n-$C_3H_7$ | $C_2H_5$ | |
| 61 | cyclohexen-1-yl-4 | 1-isopropyl-3-methyl-butadien-1,3-ylene | H | n-$C_3H_7$ | $-CH_2-CH=CH_2$ | |
| 62 | bicyclo[2,2,1]heptan-2-yl- | 1-methylethylene | H | n-$C_3H_7$ | $C_2H_5$ | 1.5230 (24) |
| 63 | bicyclo[2,2,1]heptan-2-yl- | 1-methylethylene | H | n-$C_3H_7$ | $-CH_2-CH=CH_2$ | 1.5278 (24) |
| 64 | bicyclo[2,2,1]heptan-2-yl- | 1-isopropylethylene | H | n-$C_3H_7$ | $C_2H_5$ | |
| 65 | bicyclo[2,2,1]heptan-2-yl- | 1-isopropylethylene | H | n-$C_3H_7$ | $CH_2-CH=CH_2$ | |
| 66 | bicyclo[2,2,1]heptan-2-yl- | 1-methylvinylene | H | n-$C_3H_7$ | $C_2H_5$ | |
| 67 | bicyclo[2,2,1]heptan-2-yl- | 1-methylvinylene | H | n-$C_3H_7$ | $-CH_2-CH=CH_2$ | |
| 68 | bicyclo[2,2,1]heptan-2-yl- | 1-isopropylvinylene | H | n-$C_3H_7$ | $C_2H_5$ | |
| 69 | bicyclo[2,2,1]heptan-2-yl- | 1-isopropylvinylene | H | n-$C_3H_7$ | $-CH_2-CH=CH_2$ | |
| 70 | bicyclo[2,2,1]heptan-2-yl- | 1,3-dimethylbutadien-1,3-ylene | H | n-$C_3H_7$ | $C_2H_5$ | |
| 71 | bicyclo[2,2,1]heptan-2-yl- | 1,3-dimethylbutadien-1,3-ylene | H | n-$C_3H_7$ | $-CH_2-CH=CH_2$ | |
| 72 | bicyclo[2,2,1]heptan-2-yl- | 1,3-diisopropyl-butadien-1,3-ylene | H | n-$C_3H_7$ | $C_2H_5$ | |
| 73 | bicyclo[2,2,1]heptan-2-yl- | 1,3-diisopropyl-butadien-1,3-ylene | H | n-$C_3H_7$ | $-CH_2-CH=CH_2$ | |
| 74 | bicyclo[2,2,1]heptan-2-yl- | 1-methyl-3-isopropyl-butadien-1,3-ylene | H | n-$C_3H_7$ | $C_2H_5$ | |
| 75 | bicyclo[2,2,1]heptan-2-yl- | 1-methyl-3-isopropyl-butadien-1,3-ylene | H | n-$C_3H_7$ | $-CH_2-CH=CH_2$ | |
| 76 | bicyclo[2,2,1]heptan-2-yl- | 1-isopropyl-3-methyl-butadien-1,3-ylene | H | n-$C_3H_7$ | $C_2H_5$ | |
| 77 | bicyclo[2,2,1]heptan-2-yl- | 1-isopropyl-3-methyl-butadien-1,3-ylene | H | n-$C_3H_7$ | $-CH_2-CH=CH_2$ | |
| 78 | 2,2,6-trimethylcyclohexyl-1 | 1-methylethylene | H | n-$C_3H_7$ | $-C_2H_5$ | |
| 79 | 2,2,6-trimethylcyclohexyl-1 | 1-methylethylene | H | n-$C_3H_7$ | $-CH_2-CH=CH_2$ | |
| 80 | 2,2,6-trimethylcyclohexyl-1 | 1-isopropylethylene | H | n-$C_3H_7$ | $C_2H_5$ | |
| 81 | 2,2,6-trimethylcyclohexyl-1 | 1-isopropylethylene | H | n-$C_3H_7$ | $-CH_2-CH=CH_2$ | |
| 82 | 2,2,6-trimethylcyclohexyl-1 | 1,3-dimethyltetra-methylene | H | n-$C_3H_7$ | $-C_2H_5$ | |
| 83 | 2,2,6-trimethylcyclohexyl-1 | 1,3-dimethyltetra-methylene | H | n-$C_3H_7$ | $-CH_2-CH=CH_2$ | |
| 84 | 2,2,6-trimethylcyclohexyl-1 | 1,3-diisopropyltetra-methylene | H | n-$C_3H_7$ | $C_2H_5$ | |
| 85 | 2,2,6-trimethylcyclohexyl-1 | 1,3-diisopropyltetra-methylene | H | n-$C_3H_7$ | $-CH_2-CH=CH_2$ | |
| 86 | 2,2,6-trimethylcyclohexyl-1 | 1-methylvinylene | H | n-$C_3H_7$ | $C_2H_5$ | |
| 87 | 2,2,6-trimethylcyclohexyl-1 | 1-methylvinylene | H | n-$C_3H_7$ | $-CH_2-CH=CH_2$ | |
| 88 | 2,2,6-trimethylcyclohexyl-1 | 1,3-dimethylbutadien-1,3-ylene | H | n-$C_3H_7$ | $C_3H_7$ | $C_2H_5$ |
| 89 | 2,2,6-trimethylcyclohexyl-1 | 1,3-dimethylbutadien- | H | n-$C_3H_7$ | $-CH_2-CH=CH_2$ | |
| 90 | 2,2,6-trimethylcyclohexyl-1 | 1-methyl-3-isopropyl-butadien-1,3-ylene | H | n-$C_3H_7$ | $C_2H_5$ | |
| 91 | 2,2,6-trimethylcyclohexyl-1 | 1-methyl-3-isopropyl-butadien-1,3-ylene | H | n-$C_3H_7$ | $-CH_2-CH=CH_2$ | |
| 92 | 2,2,6-trimethylcyclohexyl-1 | 1,3-diisopropyl-butadien-1,3-ylene | H | n-$C_3H_7$ | $-C_2H_5$ | |
| 93 | 2,2,6-trimethylcyclohexyl-1 | 1,3-diisopropyl-butadien-1,3-ylene | H | n-$C_3H_7$ | $-CH_2-CH=CH_2$ | |
| 94 | 1-methylcyclohexen-1-yl-4 | 2-methylethylene | H | n-$C_3H_7$ | $-C\equiv CH$ | |
| 95 | 1-methylcyclohexen-1-yl-4 | 2-methylethylene | H | $C_2H_5$ | $-C\equiv CH$ | |
| 96 | 1-methylcyclohexen-1-yl-4 sodium salt | 2-methylethylene | H | n-$C_3H_7$ | $-C_2H_5$ | |
| 97 | cyclohexylidene | methine | H | n-$C_3H_7$ | $-C\equiv CH$ | |
| 98 | cyclohexylidene sodium salt | methine | H | n-$C_3H_7$ | $-C_2H_5$ | |
| 99 | 2,2-dimethylbicyclo[2,2,1]-heptan-3-yl | methylene | H | n-$C_3H_7$ | $-C\equiv CH$ | |
| 100 | 2,2-dimethylbicyclo[2,2,1]-heptan-3-yl | methylene | H | $C_2H_5$ | $-C\equiv CH$ | |
| 101 | 2,2-dimethylbicyclo[2,2,1]-heptan-3-yl sodium salt | methylene | H | n-$C_3H_7$ | $-CH_2-CH=CH_2$ | |

-continued

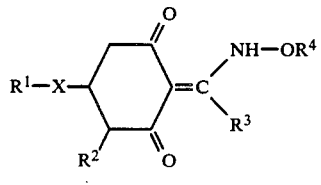

| No. | R¹ | X | R² | R³ | R⁴ | $n_D$ (at °C.) |
|---|---|---|---|---|---|---|
| 102 | cyclohexyl | 1-methylethylene | H | n-$C_3H_7$ | —$CH_2$—CH=$CH_2$ | 1.5193 (25) |
| 103 | —(4-methyl-3-cyclohexenyl | 1-methylethylene | H | n-$C_3H_7$ | —$CH_2$—CH=$CH_2$ | 1.5189 (27) |
| 104 | —(4-methyl-3-cyclohexenyl | 1-methylethylene | H | n-$C_3H_7$ | $C_2H_5$ | 1.5238* (27) |
| 105 | 3,3,4-trimethyl-4-cyclopentenyl | methylene | H | n-$C_3H_7$ | $C_2H_5$ | |
| 106 | 3,3,4-trimethyl-4-cyclopentenyl | methylene | H | n-$C_3H_7$ | —$CH_2$—CH=$CH_2$ | |
| 107 | bicyclo[2,2,1]heptyl-2 | 1-ethylvinylene | H | n-$C_3H_7$ | —$CH_2$—CH=$CH_2$ | |
| 108 | bicyclo[2,2,1]heptyl-2 | 1-ethylvinylene | H | n-$C_3H_7$ | ethyl | |
| 109 | cyclohexyl | —O—$CH_2$—$CH_2$— | H | n-$C_3H_7$ | ethyl | 1.5119 (21) |
| 110 | cyclohexyl | —O—$CH_2$—$CH_2$— | $COOCH_3$ | n-$C_3H_7$ | ethyl | 1.5072 (21) |
| 111 | cyclohexyl | —O—$CH_2$—$CH_2$— | H | n-$C_3H_7$ | —$CH_2$—CH=$CH_2$ | 1.5180 (23) |
| 112 | cyclohexyl | —CH($CH_3$)—$CH_2$—O—CH($CH_3$) | H | n-$C_3H_7$ | —$CH_2$—CH=$CH_2$ | 1.5112 (24) |
| 113 | cyclohexyl | —CH($CH_3$)—$CH_2$—O—CH($CH_3$) | H | n-$C_3H_7$ | $C_2H_5$ | 1.5069 (24) |
| 114 | cyclohexyl | —O—$CH_2$—CH($CH_3$)— | H | n-$C_3H_7$ | $C_2H_5$ | |
| 115 | cyclohexyl | —O—$CH_2$—CH($CH_3$)— | H | n-$C_3H_7$ | —CH—CH=$CH_2$ | |
| 116 | cyclododecyl | —O—$CH_2$—CH($CH_3$)— | H | n-$C_3H_7$ | $C_2H_5$ | |
| 117 | cyclododecyl | —O—$CH_2$—CH($CH_3$)— | H | n-$C_3H_7$ | —$CH_2$—CH=$CH_2$ | |
| 118 | cyclododecyl | —O—$CH_2$—$CH_2$—$CH_2$— | H | n-$C_3H_7$ | —$CH_2$—CH=$CH_2$ | |
| 119 | cyclododecyl | —O—$CH_2$—$CH_2$—$CH_2$— | H | n-$C_3H_7$ | $C_2H_5$ | |
| 120 | cyclohexyl | —O—$CH_2$—$CH_2$—$CH_2$— | H | n-$C_3H_7$ | $C_2H_5$ | |
| 121 | cyclohexyl | —O—$CH_2$—$CH_2$—$CH_2$— | H | n-$C_3H_7$ | —$CH_2$—CH=$CH_2$ | |
| 122 | 2-methylcyclohexyl | —O—$CH_2$—$CH_2$— | H | n-$C_3H_7$ | —$CH_2$—CH=$CH_2$ | |
| 123 | 2-methylcyclohexyl | —O—$CH_2$—$CH_2$— | H | n-$C_3H_7$ | $C_2H_5$ | |
| 124 | 3-methylcyclohexyl | —O—$CH_2$—$CH_2$— | H | n-$C_3H_7$ | $C_2H_5$ | |
| 125 | 3-methylcyclohexyl | —O—$CH_2$—$CH_2$— | H | n-$C_3H_7$ | —$CH_2$—CH=$CH_2$ | |
| 126 | 4-methylcyclohexyl | —O—$CH_2$—$CH_2$— | H | n-$C_3H_7$ | —$CH_2$—CH=$CH_2$ | |
| 127 | 4-methylcyclohexyl | —O—$CH_2$—$CH_2$— | H | n-$C_3H_7$ | $C_2H_5$ | 1.5038 (23) |
| 128 | 2-methoxycyclohexyl | —O—$CH_2$—$CH_2$— | H | n-$C_3H_7$ | $C_2H_5$ | |
| 129 | 2-methoxycyclohexyl | —O—$CH_2$—$CH_2$— | H | n-$C_3H_7$ | —$CH_2$—CH=$CH_2$ | |
| 130 | 3-n-butoxycyclohexyl | —O—$CH_2$—$CH_2$— | H | n-$C_3H_7$ | H | |
| 131 | 3-n-butoxycyclohexyl | —O—$CH_2$—$CH_2$— | H | n-$C_3H_7$ | $C_2H_5$ | |
| 132 | 4-isopropenylcyclohexyl | —O—$CH_2$—$CH_2$— | H | n-$C_3H_7$ | $C_2H_5$ | |
| 133 | 4-isopropylcyclohexyl | —O—$CH_2$—$CH_2$— | H | n-$C_3H_7$ | —$CH_2$—CH=$CH_2$ | |
| 134 | cyclopentyl | —O—$CH_2$—$CH_2$— | H | n-$C_3H_7$ | —$CH_2$—CH=$CH_2$ | 1.5110 (22) |
| 135 | cyclopentyl | —O—$CH_2$—$CH_2$— | H | n-$C_3H_7$ | $C_2H_5$ | 1.5052 (24) |
| 136 | cycloheptyl | —O—$CH_2$—$CH_2$— | H | n-$C_3H_7$ | $C_2H_5$ | |
| 137 | cycloheptyl | —O—$CH_2$—$CH_2$— | H | n-$C_3H_7$ | —$CH_2$—CH=$CH_2$ | |
| 138 | cyclooctyl | —O—$CH_2$—$CH_2$— | H | n-$C_3H_7$ | —$CH_2$—CH=$CH_2$ | |
| 139 | cyclooctyl | —O—$CH_2$—$CH_2$ | H | n-$C_3H_7$ | $C_2H_5$ | |
| 140 | 2-methylcyclohexyl | —O—CH($CH_3$)— | H | n-$C_3H_7$ | $C_2H_5$ | |
| 141 | 2-methylcyclohexyl | —O—CH($CH_3$)— | H | n-$C_3H_7$ | —$CH_2$—CH=$CH_2$ | |
| 142 | 3-methylcyclohexyl | —O—CH($CH_3$)— | H | n-$C_3H_7$ | —$CH_2$—CH=$CH_2$ | |
| 143 | 3-methylcyclohexyl | —O—CH($CH_3$)— | H | n-$C_3H_7$ | $C_2H_5$ | |
| 144 | 4-methylcyclohexyl | —O—CH($CH_3$)— | H | n-$C_3H_7$ | $C_2H_5$ | 1.5119 (22) |
| 145 | 4-methylcyclohexyl | —O—CH($CH_3$)— | H | n-$C_3H_7$ | —$CH_2$—CH=$CH_2$ | 1.5171 (22) |
| 146 | 2-methoxycyclohexyl | —O—CH($CH_3$)— | H | n-$C_3H_7$ | —$CH_2$—CH=$CH_2$ | |
| 147 | 2-methoxycyclohexyl | —O—CH($CH_3$)— | H | n-$C_3H_7$ | $C_2H_5$ | |
| 148 | 3-n-butoxycyclohexyl | —O—CH($CH_3$)— | H | n-$C_3H_7$ | $C_2H_5$ | |
| 149 | 3-n-butoxycyclohexyl | —O—CH($CH_3$)— | H | n-$C_3H_7$ | —$CH_2$—CH=$CH_2$ | |
| 150 | 4-isopropenylcyclohexyl | —O—CH($CH_3$)— | H | n-$C_3H_7$ | —$CH_2$—CH=$CH_2$ | |
| 151 | 4-isopropenylcyclohexyl | —O—CH($CH_3$)— | H | n-$C_3H_7$ | $C_2H_5$ | |
| 152 | cyclopentyl | —O—CH($CH_3$)— | H | n-$C_3H_7$ | $C_2H_5$ | 1.5088 (23) |
| 153 | cyclopentyl | —O—CH($CH_3$)— | H | n-$C_3H_7$ | —$CH_2$—CH=$CH_2$ | 1.5140 (24) |
| 154 | cycloheptyl | —O—CH($CH_3$)— | H | n-$C_3H_7$ | —$CH_2$—CH=$CH_2$ | 1.5154 (24) |
| 155 | cycloheptyl | —O—CH($CH_3$)— | H | n-$C_3H_7$ | $C_2H_5$ | 1.5099 (24) |
| 156 | cyclooctyl | —O—CH($CH_3$)— | H | n-$C_3H_7$ | $C_2H_5$ | 1.5132 (22) |
| 157 | cyclooctyl | —O—CH($CH_3$)— | H | n-$C_3H_7$ | —$CH_2$—CH=$CH_2$ | 1.5183 (22) |
| 158 | 2,2-dichlorocyclopropyl | —$CH_2$—O—CH($CH_3$)—$CH_2$— | H | n-$C_3H_7$ | —$CH_2$—CH=$CH_2$ | |
| 159 | 2,2-dichlorocyclopropyl | —$CH_2$—O—CH($CH_3$)—$CH_2$— | H | n-$C_3H_7$ | $C_2H_5$ | |
| 160 | 2,4,4-trimethyl-1-cyclohexenyl | —$CH_2$—O—CH($CH_3$)—$CH_2$— | H | n-$C_3H_7$ | $C_2H_5$ | |
| 161 | 2,4,4-trimethyl-1-cyclohexenyl | —$CH_2$—O—CH($CH_3$)—$CH_2$— | H | n-$C_3H_7$ | —$CH_2$—CH=$CH_2$ | |
| 162 | cyclohexyl | —$CH_2$—O—CH($CH_3$)—$CH_2$— | H | n-$C_3H_7$ | —$CH_2$—CH=$CH_2$ | |
| 163 | cyclohexyl | —$CH_2$—O—CH($CH_3$)—$CH_2$— | H | n-$C_3H_7$ | $C_2H_5$ | |
| 164 | cyclohexyl | —$CH_2$—O—CH($CH_3$)— | H | n-$C_3H_7$ | $C_2H_5$ | |
| 165 | cyclohexyl | —$CH_2$—O—CH($CH_3$)— | H | n-$C_3H_7$ | —$CH_2$—CH=$CH_2$ | |
| 166 | cyclohexyl | —O—$CH_2$—$CH_2$—O—$CH_2$—$CH_2$— | H | n-$C_3H_7$ | $C_2H_5$ | |
| 167 | cyclohexyl | —O—$CH_2$—$CH_2$—O—$CH_2$—$CH_2$— | H | n-$C_3H_7$ | —$CH_2$—CH=$CH_2$ | |
| 168 | cyclohexyl | —S—$CH_2$—$CH_2$—S—$CH_2$—$CH_2$— | H | n-$C_3H_7$ | —$CH_2$—CH=$CH_2$ | |
| 169 | cyclohexyl | —S—$CH_2$—$CH_2$—S—$CH_2$—$CH_2$— | H | n-$C_3H_7$ | $C_2H_5$ | |
| 170 | cyclohexyl | —S—$CH_2$—$CH_2$—O—$CH_2$—$CH_2$— | H | n-$C_3H_7$ | $C_2H_5$ | |
| 171 | cyclohexyl | —S—$CH_2$—$CH_2$—O—$CH_2$—$CH_2$— | H | n-$C_3H_7$ | —$CH_2$—CH=$CH_2$ | |
| 172 | cyclohexyl | —S—CH($CH_3$)—$CH_2$— | H | n-$C_3H_7$ | $C_2H_5$ | 1.5295 (22) |
| 173 | cyclohexyl | —S—CH($CH_3$)—$CH_2$— | H | n-$C_3H_7$ | —$CH_2$—CH=$CH_2$ | |

-continued

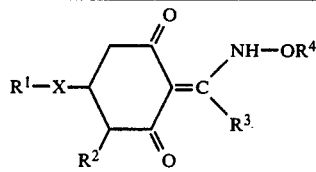

| No. | R¹ | X | R² | R³ | R⁴ | $n_D$ (at °C.) |
|---|---|---|---|---|---|---|
| 174 | cyclohexyl | —S—CH$_2$—CH$_2$— | H | n-C$_3$H$_7$ | —CH$_2$—CH=CH$_2$ | |
| 175 | cyclohexyl | —S—CH$_2$—CH$_2$— | H | n-C$_3$H$_7$ | C$_2$H$_5$ | |
| 176 | 2,2,4-trimethyl-3-cyclohexenyl | methylene | H | n-C$_3$H$_7$ | C$_2$H$_5$ | |
| 177 | 2,2,4-trimethyl-3-cyclohexenyl | methylene | H | n-C$_3$H$_7$ | —CH$_2$—CH=CH$_2$ | |
| 178 | bicyclo[2,2,1]heptyl-2 | 1-ethylvinylene | H | n-C$_3$H$_7$ | —CH$_2$—CH=CH$_2$ | |
| 179 | bicyclo[2,2,1]heptyl-2 | 1-ethylvinylene | H | n-C$_3$H$_7$ | C$_2$H$_5$ | |
| 180 | bicyclo[2,2,1]heptyl-2 | 1,4-dimethylbutadien-1,3-ylene | H | n-C$_3$H$_7$ | C$_2$H$_5$ | |
| 181 | bicyclo[2,2,1]heptyl-2 | 1,4-dimethylbutadien-1,3-ylene | H | n-C$_3$H$_7$ | —CH$_2$—CH=CH$_2$ | |
| 182 | bicyclo[2,2,1]heptyl-2 | 1,4-dimethylbuten-3-ylene | H | n-C$_3$H$_7$ | —CH$_2$—CH=CH$_2$ | |
| 183 | bicyclo[2,2,1]heptyl-2 | 1,4-dimethylbuten-3-ylene | H | n-C$_3$H$_7$ | —C$_2$H$_5$ | |
| 184 | 2,2,3-trimethylcyclopent-3-en-1-yl | methylene | H | n-C$_3$H$_7$ | —C$_2$H$_5$ | 1.515 (20) |
| 185 | 2,2,3-trimethylcyclopent-3-en-1-yl | methylene | H | n-C$_3$H$_7$ | —CH$_2$—CH=CH$_2$ | 1.521 (20) |
| 186 | 2,2,3-trimethylcyclopent-3-en-1-yl | methylene | H | n-C$_3$H$_7$ | —CH$_2$—C≡CH | 1.5230 (26) |
| 187 | 2-methoxycyclohexyl | O—CH(CH$_3$)— | COOCH$_3$ | n-C$_3$H$_7$ | —CH$_2$—CH=CH$_2$ | 1.5132 (23) |

*angle of rotation alpha$_D^{20}$ = −33.8° in methanol

APPLICATION

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably from 0.5 to 90, wt% of active ingredient.

The active ingredients are applied to the plants or soil for instance by watering, broadcasting, dusting, spraying or atomizing, by coating plants with them, or by introducing them into the irrigation system.

The agents may be applied pre- or postemergence. Preferably, the novel active ingredients are applied after emergence of the unwanted plants. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved, the plants to be combated, and the growth stage of the plants, and varies from 0.05 to 5 kg/ha and more, but is preferably from 0.1 to 5 kg/ha.

The influence of representatives of the novel cyclohexane-1,3-dione derivatives on the growth of unwanted and crop plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce geermination and growth and to activate the chemical agents. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants used for the postemergence treatment were grown in a peat-enriched substrate to ensure better growth than is possible in a sandy loam. For this treatment, either plants which had been sown directly in the pots and grown there were selected, or plants which had been grown separately as seedlings and transplanted to the experiment vessels a few days before treatment. No covers were placed on the pots in this treatment method. The application rates for postemergence treatment varied from ingredient to ingredient, and were from 1.0 and 3.0 kg of active ingredient per hectare.

The following compounds were used for comparison purposes:

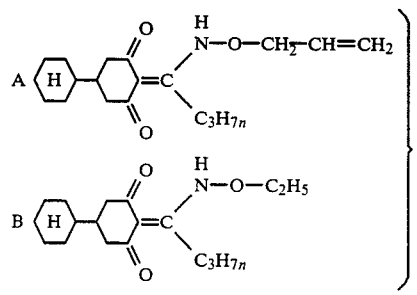

(Japanese Preliminary Published Application 54-19,945)

These compounds were applied at a rate of 0.25 kg/ha. At this rate, compounds A and B caused damage to wheat which was no longer acceptable.

The following test plants were used in the experiments:

| botanical name | Common name |
| --- | --- |
| Alopecurus myosuroides | blackgrass |
| Avena fatua | wild oats |
| Echinochloa crus-galli | barnyardgrass |
| Glycine max. | soybeans |
| Lolium multiflorum | Italian ryegrass |
| Setaria italica | foxtail |
| Triticum aestivum | wheat |

The pots were set up in the greenhouse—species from warmer areas at from 20° to 35° C., and species from moderate climates at 10° to 20° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

On preemergence application in the greenhouse, compounds nos. 1, 20, and 25, applied at a rate of 3.0 kg/ha, had a considerable herbicidal action on grass species. The same is true of the postemergence application of these compounds (cf. Table 1).

In investigations in the greenhouse into selective herbicidal action, compounds nos. 1 and 20, at 1.0 kg/ha, combated unwanted grass species quite well (Table 2). They caused no damage to the crop plants soybeans and wheat. Although the prior art comparative agents, at 0.25 kg/ha, had a similar herbicidal action, they caused heavy and no longer acceptable damage to wheat. It was not possible to reduce the application rate further because of insufficient herbicidal action.

The Tables 3-5 show the selective control of unwanted grasses in cereals and other crops. With compounds nos. 172, 157 and 145, the damage to crop plants ranged from 0 to 10%. In contrast, with the prior art materials the damage ranged from 0 to 100%.

In view of the good tolerance of the herbicides according to the invention, or agents containing them, by numerous broadleaved and other crops, and the numerous application methods possible, they may be used in a large number of crops for removing unwanted plant growth.

The following crops may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rape seed |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, | coffee plants |

| Botanical name | Common name |
|---|---|
| Coffea liberica) | |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum | cotton |
| (Gossypium arboreum | |
| Gossypium herbaceum | |
| Gossypium vitifolium) | |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum | tobacco |
| (N. rustica) | |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum | parsley |
| spp. tuberosum | |
| Picea abies | Norway spruce |
| Abies alba | fir trees |
| Pinus spp. | pine trees |
| Pisum sativum | English peas |

| Botanical name | Common name |
|---|---|
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |

To increase the spectrum of action and to achieve synergistic effects, the novel cyclohexane-1,3-dione derivatives may be mixed and applied together with numerous representatives of other herbicidal or growth-regulating active ingredient groups. Examples of suitable mixture components are diazines, 4H-3,1-benzoxazine derivatives, 2,6-dinitroanilines, N-phenylcarbamates, thiolcarbamates, halocarboxylic acids, triazines, amides, ureas, diphenyl ethers, triazinones, uracils, benzofuran derivatives, etc.

It may also be useful to apply the novel compounds, either on their own or combined with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

TABLE 1

Action on plants from the grass family on pre- and postemergence application of 3.0 kg/ha in the greenhouse

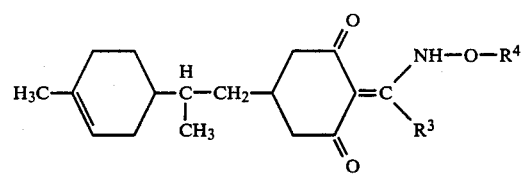

| | | | Test plants and % damage | | | |
|---|---|---|---|---|---|---|
| Active ingredient no. | $R^3$ | $R^4$ | Preemergence | | Postemergence | |
| | | | Echinoch. c.g. | Lolium multifl. | Echinoch. c.g. | Lolium multifl. |
| 20 (S configuration) | n-$C_3H_7$ | —$CH_2$—CH=$CH_2$ | 98 | 100 | 100 | 90 |
| 1 (S configuration) | n-$C_3H_7$ | $C_2H_5$ | 100 | 100 | 100 | 90 |
| 25 | n-$C_3H_7$ | —$CH_2$CH=CHCl | 80 | 100 | 100 | 100 |

TABLE 2

Selective control of unwanted grasses in cereals and other crops on postemergence treatment in the greenhouse

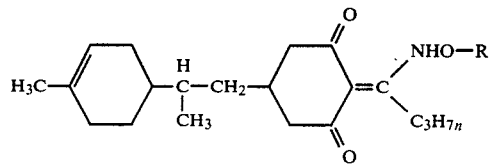

| Active ingredient no. | R | kg/ha | Glycine max. | Triticum aestivum | Alopecur. myos. | Avena fatua | Setaria italica |
|---|---|---|---|---|---|---|---|
| 1 according to invention | $C_2H_5$ | 1.0 | 0 | 0 | 98 | 80 | 90 |
| 20 to invention | $-CH_2-CH=CH_2$ | 1.0 | 0 | 0 | 80 | 95 | 98 |
| A (prior art) | — | 0.25 | 0 | 60 | 80 | 80 | 100 |
| B (prior art) | — | 0.25 | 0 | 45 | 95 | 80 | 90 |

TABLE 3

Selective control of unwanted grasses in cereals and other crops on postemergence application in the greenhouse

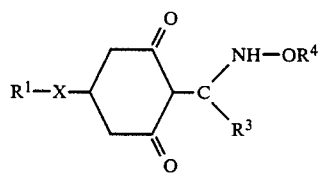

| Active ingredient no. | $R^1-X-$ | $R^3$ | $R^4$ | kg/ha a.i. | Glycine* max | Beta vulgaris | Triticum** aestivum | Alopecurus myosuroid. | Avena fatua | Lolium multiflorum |
|---|---|---|---|---|---|---|---|---|---|---|
| 172 | cyclohexyl-S-CH(CH$_3$)-CH$_2-$ | $nC_3H_7$ | $C_2H_5$ | 0,125 | 0 | 0 | 10 | 89 | 99 | 98 |
| A prior art | naphthyl- | $n$-$C_3H_7$ | $CH_2-CH=CH_2$ | 0,125 | 0 | 0 | 62 | 84 | 80 | 90 |
| B prior art | naphthyl- | $n$-$C_3H_7$ | $C_2H_5$ | 0,125 | 0 | 0 | 52 | 80 | 75 | 89 |

*variety SRF 45
**variety Kolibri

TABLE 4

Selective control of unwanted grasses in cereals on postemergence application in the greenhouse

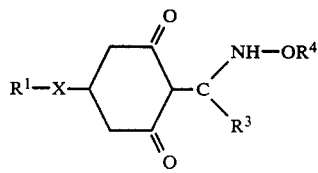

| Active ingredient no. | $R^1-X-$ | $R^3$ | $R^4$ | kg/ha a.i. | Hordeum* vulgare | Triticum** aestivum | Alopecurus myosuroides | Avena fatua |
|---|---|---|---|---|---|---|---|---|
| 157 | cycloheptyl-OCH(CH$_3$)- | $n$-$C_3H_7$ | $CH_2CH=CH_2$ | 0,5 | 10 | 0 | 97 | 100 |

TABLE 4-continued

Selective control of unwanted grasses in cereals on postemergence application in the greenhouse

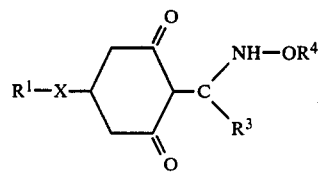

| Active ingredient no. | R¹—X— | R³ | R⁴ | kg/ha a.i. | Hordeum* vulgare | Triticum** aestivum | Alopecurus myosuroides | Avena fatua |
|---|---|---|---|---|---|---|---|---|
| A } prior art | (decalinyl) | n-C₃H₇ | CH₂—CH=CH₂ | 0,5 | 100ᵃ | 90 | 87 | 80 |
| B } | (decalinyl) | n-C₃H₇ | C₂H₅ | 0,5 | 95ᵃ | 90 | 91 | 88 |

*variety Steina
**variety Ralle
ᵃwith 0,25 kg/ha

TABLE 5

Control of unwanted grasses in rice with reference to *Echinochloa crus-galli* on postemergence application in the green house

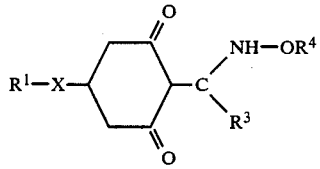

| Active ingredient no. | R¹—X— | R³ | R⁴ | kg/ha a.i. | Oryza sativa* | Echinochloa c.g. |
|---|---|---|---|---|---|---|
| 145 | (cyclohexyl-CH₃-O-CH-) | nC₃H₇ | —CH₂—CH=CH₂ | 0,25 | 5 | 95 |
| A } prior art | (decalinyl) | n-C₃H₇ | CH₂—CH=CH₂ | 0,25 | 59 | 83 |
| B } | (decalinyl) | n-C₃H₇ | C₂H₅ | 0,25 | 70 | 91 |

*variety Girona

We claim:

1. A cyclohexane-1,3-dione derivative of the formula

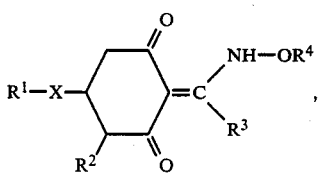

where $R^1$ is cycloalkyl of 3 to 12 carbon atoms which may or may not be olefinically mono-unsaturated, can be substituted by not more than 3 methyl or ethyl groups or by one vinyl, methylvinyl or allyl group, 1 or 2 chlorine atoms or one alkoxy group of 1 to 4 carbon atoms and can be bridged by an alkylene chain of not more than 4 carbon atoms, X is alkylene of 1 to 5 carbon atoms, which contains 1 or 2 heteroatoms selected from sulfur and oxygen, which may be mono-unsaturated and which may be substituted by 1 to 3 alkyl groups of 1 to 3 carbon atoms, $R^2$ is hydrogen or alkoxycarbonyl where alkoxy is of 1 to 2 carbon atoms, $R^3$ is alkyl of 1 to 4 carbon atoms, $R^4$ is alkyl of 1 to 3 carbon atoms, alkenyl of 3 or 4 carbon atoms, propargyl or haloalkenyl of 3 or 4 carbon atoms and 1 to 3 halogen atoms, or a salt thereof.

2. A herbicide containing conventional additives and, as active ingredient, from 0.5 to 90 wt% of a cyclohexane-1,3-dione derivative of the formula I as claimed in claim 1.

3. A process for combating the growth of unwanted plants, wherein the unwanted plants or the area to be kept free from unwanted plant growth are treated with a herbicidally effective amount of a cyclohexane-1,3-dione derivative of the formula I as claimed in claim 1.

* * * * *